United States Patent
Soykan et al.

(10) Patent No.: US 6,236,889 B1
(45) Date of Patent: May 22, 2001

(54) METHOD AND APPARATUS FOR ACCOUSTICALLY COUPLING IMPLANTABLE MEDICAL DEVICE TELEMETRY DATA TO A TELEPHONIC CONNECTION

(75) Inventors: Orhan Soykan, New Brighton; William J. Combs, Eden Prairie; Michael B. Shelton, Minneapolis, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/235,444

(22) Filed: Jan. 22, 1999

(51) Int. Cl.[7] .................................................. A61N 1/08
(52) U.S. Cl. ............................... 607/30; 607/60; 607/32; 128/904
(58) Field of Search ................................ 607/30, 32, 59, 607/60; 128/904

(56) References Cited

U.S. PATENT DOCUMENTS

| | | | |
|---|---|---|---|
| 4,159,018 | * 6/1979 | Brastad | 607/32 |
| 4,556,063 | 12/1985 | Thompson et al. | |
| 4,681,111 | * 7/1987 | Silvian | |
| 4,821,723 | 4/1989 | Baker et al. | |
| 5,144,949 | 9/1992 | Olson | |
| 5,158,078 | 10/1992 | Bennett et al. | |
| 5,199,428 | 4/1993 | obel et al. | |
| 5,312,453 | 5/1994 | Shelton et al. | 607/19 |
| 5,314,430 | 5/1994 | Bardy | 607/5 |
| 5,330,507 | 7/1994 | Schwartz | 607/14 |
| 5,331,966 | 7/1994 | Bennett et al. | |
| 5,354,316 | 10/1994 | Keimel | 607/15 |
| 5,433,736 | * 7/1995 | Nilsson | 607/32 |

* cited by examiner

Primary Examiner—Scott M. Getzow
(74) Attorney, Agent, or Firm—Michael B. Atlass; Harold R. Patton

(57) ABSTRACT

An apparatus and method for communicating acoustic telemetry data produced by an implantable medical device over a communication channel includes a signal generator, a modulator, and an acoustic transmitter each provided in the implantable medical device. The modulator modulates a carrier signal with an information signal representative of information acquired or produced by the implantable medical device so as to produce a modulated information signal. The modulated information signal may have a frequency content that is readily accommodated by a public exchange communication channel. The transmitter transmits the modulated information signal as an acoustic information signal in a form communicable over the communication channel. The acoustic information signal may constitute telephonic tones which are directly communicable over a conventional telephone connection. The acoustic information signal may constitute digital telephonic tones each having a frequency and format that conforms to one or more telephony standards. In an embodiment in which the communication channel constitutes a public exchange communication channel, the acoustic information signal preferably has a frequency content that is band limited by an audio bandwidth of the public exchange communication channel. A number of different modulation techniques may be employed, including phase modulation, amplitude modulation or frequency modulation. Implantable medical devices which may incorporate telemetry circuitry of the present invention include a pacemaker, a pacemaker/cardioverter/defibrillator (PCD), an oxygen sensing device, an implantable hemodynamic monitor, a muscle stimulator device or a nerve stimulator device.

29 Claims, 5 Drawing Sheets

METHOD AND APPARATUS FOR ACCOUSTICALLY COUPLING IMPLANTABLE MEDICAL DEVICE TELEMETRY DATA TO A TELEPHONIC CONNECTION

FIELD OF THE INVENTION

The present invention relates generally to implantable medical devices. More particularly, the present invention pertains to systems and methods for facilitating transmission of acoustic telemetry data between an implantable medical device and a communication channel.

BACKGROUND OF THE INVENTION

Various telemetry techniques have been developed to facilitate transmission of information between an implantable medical device and an external programming unit. A typical programming unit is understood in the art to constitute a sophisticated and expensive system that provides for the downlinking and uplinking of electromagnetic signal information between an implantable medical device and the programming unit. Although such a conventional telemetry approach has been well received and provides for excellent data rates, it is appreciated in the industry that the high cost and complexity of a typical programming unit often precludes use of such systems in certain applications.

For many patients provided with an implantable medical device, continuous and/or follow-up monitoring is considered by many clinicians as necessary to the process of fully evaluating the condition and progress of the patient. A conventional monitoring approach that employs a programming unit typically requires the patient to travel from home to a physician's office or a health care clinic. It can be appreciated that patients requiring such monitoring are typically incapacitated to some degree, and traveling to a distant health facility often represents a sizeable undertaking.

A patient who is provided with an implantable medical device designed to communicate with a programming unit or other communication system interface (e.g., modem) is often limited in terms of freedom of movement, particularly during periods of evaluation and diagnosis. The inherent inconvenience associated with conventional implantable medical device monitoring techniques may dissuade patients from participating in needed medical evaluations.

There is a need for improved ways of obtaining telemetry data from an implantable medical device that are lower in cost, simple to use, and provide for increased freedom of patient movement as compared to conventional telemetry approaches. The present invention fulfills these and other needs.

SUMMARY OF THE INVENTION

The present invention is directed to an apparatus and method for communicating acoustic telemetry data produced by an implantable medical device over a communication channel. A signal generator is provided in the implantable medical device and generates a carrier signal. A modulator, also provided in the implantable medical device, impresses an information signal representative of information acquired or produced by the implantable medical device on the carrier signal so as to produce a modulated information signal. The modulated information signal may have a frequency content that is readily accommodated by a public exchange communication channel. A transmitter, provided at the implantable medical device, transmits the modulated information signal as an acoustic information signal preferably in a form communicable over the communication channel.

The acoustic information signal may constitute telephonic tones which are directly communicable over a conventional telephone connection. The telephonic tones typically include a first tone representative of a first information signal state and a second tone representative of a second information signal state. The acoustic information signal may, for example, constitute digital telephonic tones each having a frequency and format that conforms to one or more telephony standards. In an embodiment in which the communication channel constitutes a public exchange communication channel, the acoustic information signal preferably has a frequency content that is band limited by an audio bandwidth of the public exchange communication channel.

The modulator may impress the information signal on the carrier signal using a number of different modulation techniques, including phase modulation, amplitude modulation or frequency modulation. For example, the modulator may modulate the carrier signal with the information signal using phase key shifting modulation, amplitude key shifting modulation or frequency key shifting modulation techniques. The transmitter includes an electrical-to-acoustic transducer, such as a piezoelectric crystal, a speaker or a microphone. The acoustic information signal is communicable over a variety of communication mediums, including an analog communication channel, a digital communication channel, and optical communication channel, a microwave communication channel or a satellite communication channel, for example.

An implantable medical device may further be provided with an acoustic receiving device for purposes of downlinking acoustic telemetry commands and information from a communication channel to the implantable medical device. In such an embodiment, an acoustic transmitter and an acoustic receiver may be provided in the implantable medical device or, alternatively, a single acoustic transceiver may be employed. A demodulator is provided in the implantable medical device for demodulating a modulated signal received from the communication channel.

An implantable medical device that incorporates an acoustic telemetry production and transmission system of the present invention may further be provided with conventional electromagnetic (e.g., radio frequency) telemetry components for purposes of providing enhanced functionality and data exchange capabilities. Bi-directional communication of implantable medical device (IMD) telemetry data through use of electromagnetic signals may be accomplished using various known techniques. The additional telemetry circuitry may be employed to facilitate communication of electromagnetic information signals of varying types between the implantable medical device and a public exchange communication system.

Embodiments of the systems and methods of the present invention may be incorporated into a wide variety of implantable medical devices. Examples of such implantable medical devices include a pacemaker, a pacemaker/cardioverter/defibrillator (PCD), an oxygen sensing device, an implantable hemodynamic monitor, a muscle stimulator device or a nerve stimulator device, for example.

The above summary of the present invention is not intended to describe each embodiment or every implementation of the present invention. Advantages and attainments, together with a more complete understanding of the invention, will become apparent and appreciated by refer-

Figure 1:
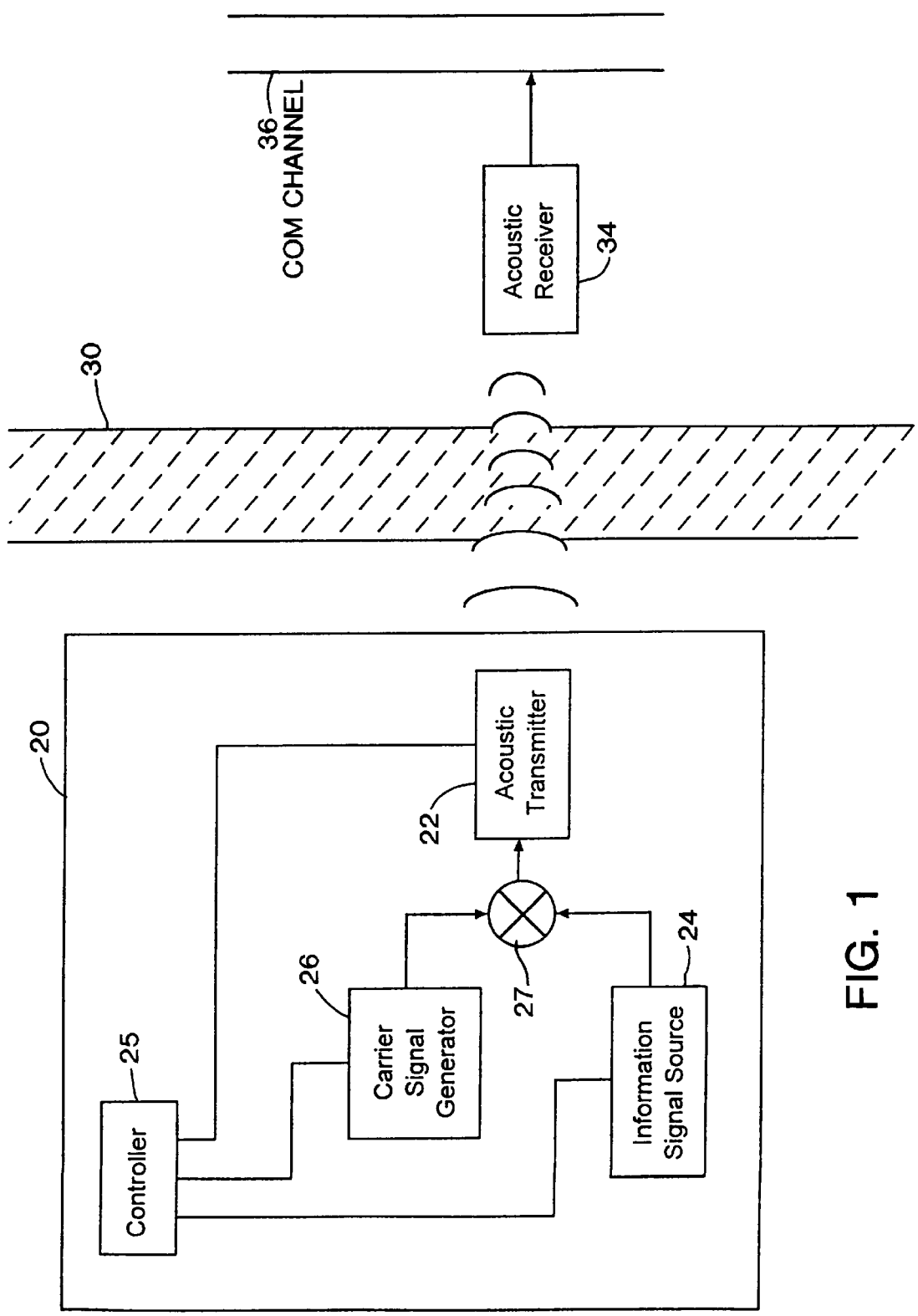
FIG. 1 is a block diagram of an implantable medical device provided with telemetry circuitry in accordance with the present invention.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

FIG. 1 is a block diagram of an apparatus for acoustically communicating telemetry data produced by an implantable medical device through the body and over a communication link, such as a telephonic connection for example. The implantable medical device 20 shown in FIG. 1, as well as in other Figures, is intended to represent any of a wide variety of devices which may be implanted in a human body, typically for purposes of monitoring or moderating one or more physiologic conditions.

In general, the implantable medical device 20 shown in the Figures includes a hermetically-sealed enclosure which may include various elements, such as an electrochemical cell (e.g., a lithium based battery) and circuitry that controls device/sensor operations and records sensor data. Implantable medical device 20 further includes circuitry for generating an information signal preferably of a form readily communicable over a communication link, such as a digital or analog telephonic link, and circuitry for transmitting information signals acoustically from the device 20 and through the body for reception by an acoustic receiver coupled to the communication link. Implantable medical device 20 may further include circuitry for receiving downlinked acoustic telemetry data from an external acoustic transmitter coupled to the communication link, in addition to other elements.

Concerning the particular embodiment depicted in FIG. 1, implantable medical device 20 includes, among other elements, a carrier signal generator 26 and an information signal source 24. Carrier signal generator 26 and information signal source 24 are coupled to a modulator 27, the output of which is coupled to an acoustic transmitter 22. A controller 25, such as a microcontroller or microprocessor for example, coordinates the operation of the carrier signal generator 26, information signal source 24, and acoustic transmitter 22.

In general terms, an information signal provided by information signal source 24 is used by modulator 27 to modulate a carrier signal produced by carrier signal generator 26. The information signal source 24 provides an information signal which may be representative of a wide variety of information produced or acquired by implantable medical device 20. Examples of such information include physiologic sensor data, battery status data, device/sensor operational status and error status information, pacing threshold status data, pacing and sensing status data, pacemaker lead status information, and baseline ECG data.

The modulated signal is communicated from modulator 27 to acoustic transmitter 22 which, in turn, transmits the modulated signal as an acoustic signal from implantable medical device 20 and through body tissue. The acoustic signal transmitted by acoustic transmitter 22 may be received by an acoustic receiver 34 situated external to the body. The acoustic signal received by acoustic receiver 34 may be transmitted in digital, analog or optical form to a local or remote site via a suitable communication channel 36.

An important aspect of the telemetry approach according to the principles of the present invention concerns the production of a modulated signal in-situ the implantable medical device 20 and, consequently, in-situ the body. The modulated signal may be produced in accordance with various known amplitude, frequency, or phase modulation techniques, and is preferably of a form which is readily communicable over communication channel 36. Producing physiologic telemetry data in accordance with the principles of the present invention substantially reduces the complexity, and thus the cost, of the device or circuitry the receives the modulated acoustic signal produced by the implantable medical device.

By way of example, a prior art approach typically requires use of a modulator device (e.g., modulator/demodulator or modem) connected between an acoustic receiver that receives an acoustic signal from the implantable medical device and a telephonic line. The modulator device is required to produce a modulated signal suitable for transmission over a telephonic line. In stark contrast, an acoustic telemetry approach consistent with the principles of the present invention wholly obviates the need for an external modulator device, such as a modem, as the modulated signal is produced in-situ the implantable medical device 20 and preferably in a form readily communicable over a telephonic or other communication link.

It will be appreciated that the elimination of such an external modulation device provides for a significantly less complex and lower cost approach to effecting remote communication of IMD telemetry data. By way of example, and in accordance with one embodiment of the present invention which will be described in detail hereinbelow, the receiver portion of a standard telephone handset, when positioned on or near the body proximate the implantable medical device 20, may be used to receive modulated acoustic IMD telemetry signals produced by implantable medical device 20 for real-time transmission over communication channel 36 for reception at a remote site. In accordance with this embodiment, a modem or similar modulator device, which is generally required using a prior art approach, is not needed.

Figure 2:
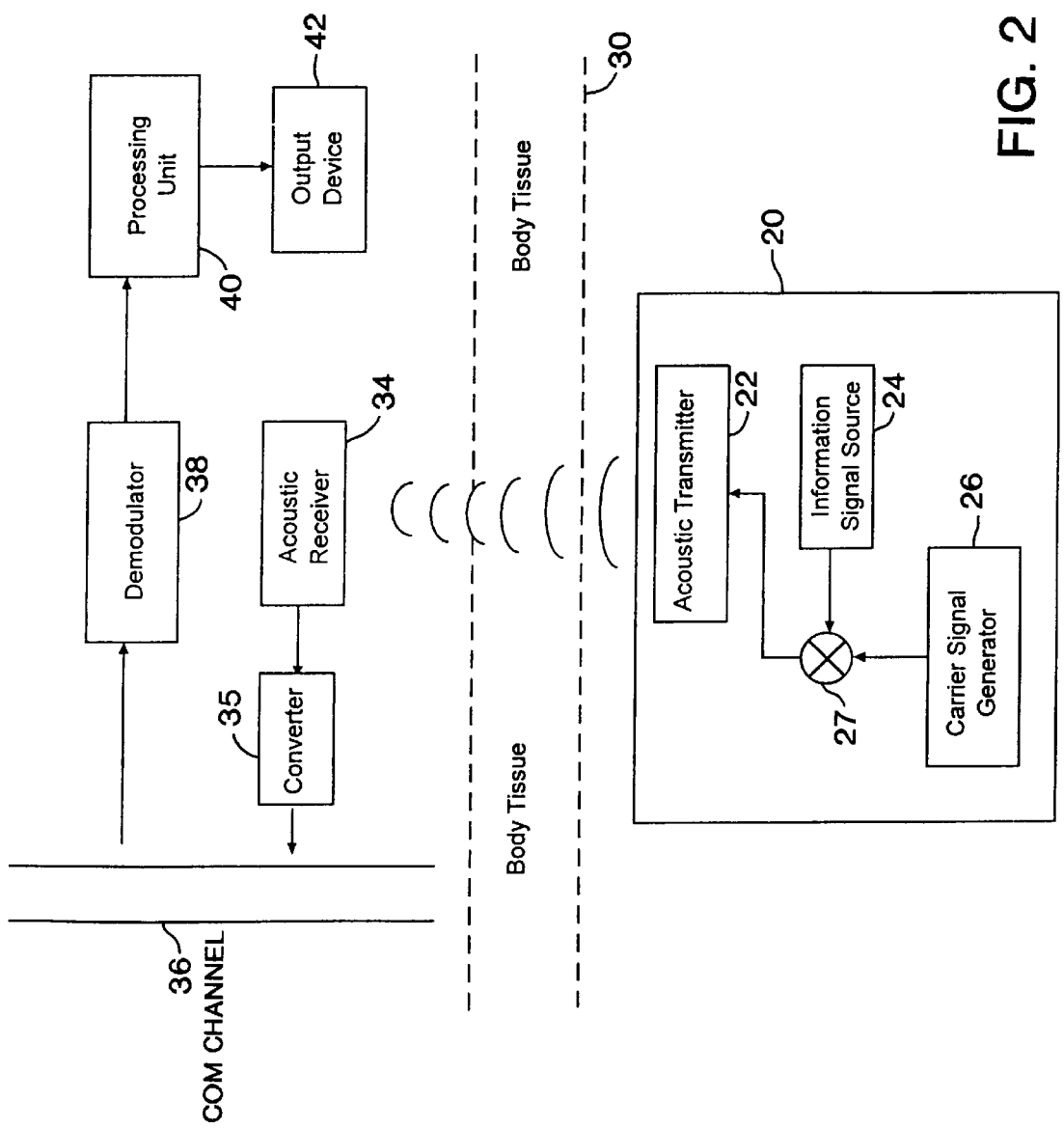
FIG. 2 is a block diagram of an implantable medical device communicating with a communication system using a telemetry approach consistent with the principles of the present invention.

FIG. 2 is an illustration of another embodiment of the present invention which shows additional elements of a system for communicating acoustic IMD telemetry data from an implantable medical device 20 to a remote processing unit 40 via a communication channel 36. In accordance with the embodiment depicted in FIG. 2, an implantable medical device 20 generates a modulated IMD signal containing information acquired by or produced within the device 20. The modulated IMD signal is transmitted in acoustic form through intervening body tissue 30 between implantable medical device 20 and acoustic receiver 34. In this embodiment, the acoustic receiver 34 communicates the modulated IMD signal to communication channel 36 via a converter 35.

It may be desirable to further process the received IMD telemetry signals prior to transmission over certain communication channels, such as fiber optic, satellite, microwave, network (e.g., the Internet or an ATM network) or high speed digital communication lines for example. Converter 35 represents a device that converts the modulated IMD signal received from acoustic receiver 34 to a form suitable for transmission over a particular communication channel 36. Converter 35 may also be representative of an amplifier which amplifies the received modulated IMD signal prior to transmission over communication channel 36. Converter 35 may further be representative of circuitry that conditions the received modulated IMD signal in a manner that facilitates transmission of the modulated IMD signal over communication channel 36. It will be understood that for many applications, converter 35 may not be desired or required.

The modulated IMD signal is directed from communication channel 36 to a remotely situated processing unit 40 via a demodulator 38 coupled to communication channel 36. Demodulator 38 converts the modulated IMD signal to a form suitable for reception by processing unit 40. For example, demodulator 38 may extract the information signal component of the modulated IMD signal using an appropriate demodulation approach. In one embodiment, the extracted information signal component is provided in digital form and may be readily operated on by processing unit 40. In an embodiment in which the extracted information signal component is provided in analog form, demodulator 38 or, alternatively, processing unit 40, converts the analog signal component to a corresponding digital signal component, typically through employment of an analog-to-digital converter. The information signal component received by processing unit 40 in either real-time or non-real-time may be stored in a database and/or processed for presentation or display using an appropriate output device 42, such as a display, a charting device or other printing device, for example.

As was previously discussed, an important aspect of a telemetry approach according to the principles of the present invention concerns the production of a modulated signal in-situ the implantable medical device 20 which is preferably readily communicable over communication channel 36. The modulated signal transmitted by implantable medical device 20 may be produced in accordance with various known amplitude, frequency, or phase modulation techniques. Although a number of known modulation techniques may be employed to produce a modulated IMD signal suitable for acoustic transmission, the inventors have found that the unusual environment within which a device embodying the principles of the present invention operates complicates the task of implementing an effective telemetry approach. Further, the characteristics of the subject communication channel must generally be take into account when implementing a particular modulation approach.

Figure 3:
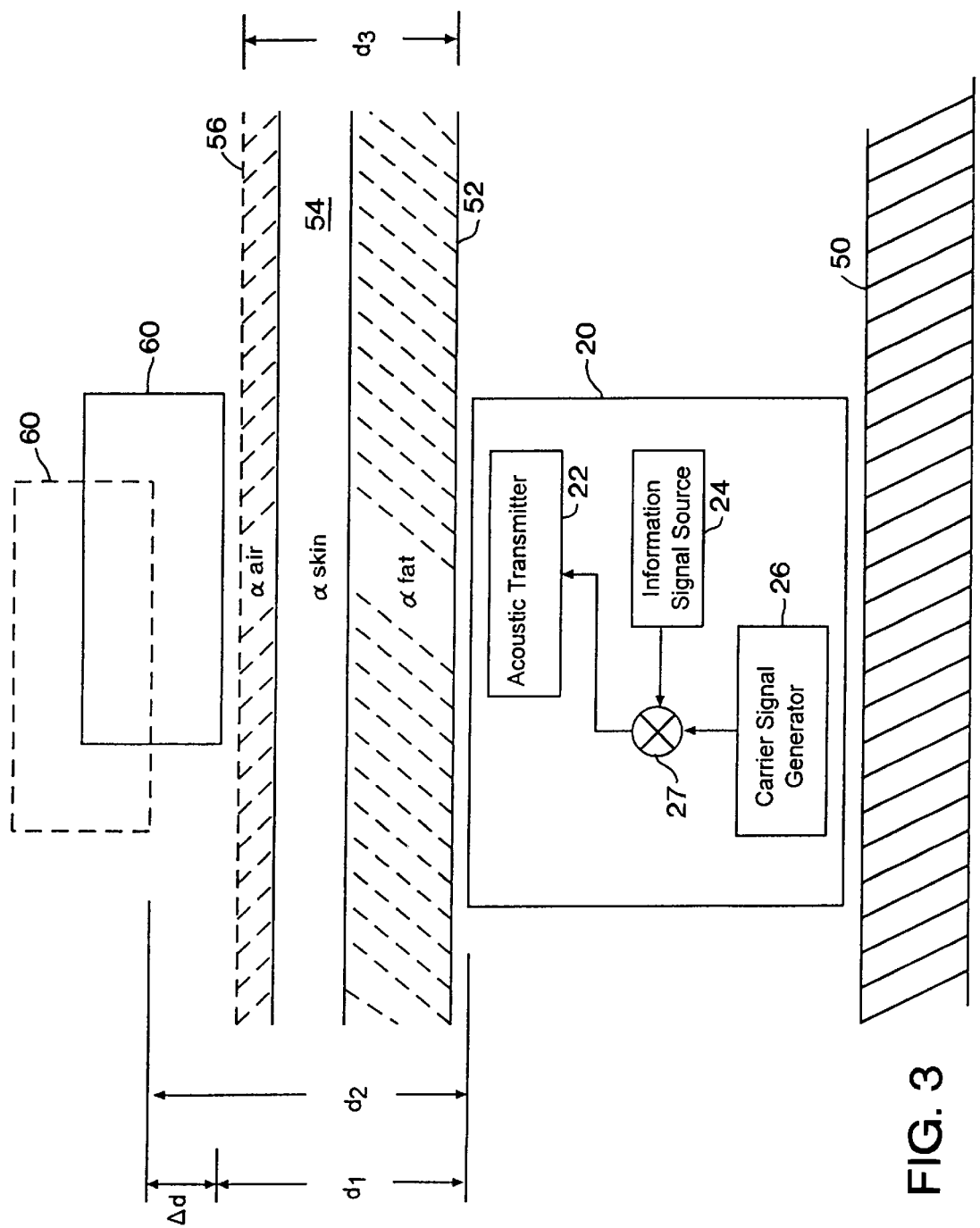
FIG. 3 illustrates various environmental conditions and constraints impacting the use of an implantable medical device provided with telemetry circuitry in accordance with the present invention.

FIG. 3 is useful for purposes of describing an environment within which an implantable medical device embodying the principles of the present invention typically operates. FIG. 3 is a generalized depiction of an implantable medical device 20 implanted in the body between muscle tissue 50 and fat tissue 52. Shown above the layer of fat tissue 52 is a skin layer 54. An acoustic receiver 60 is shown situated above the layer of skin 54. A modulated acoustic IMD signal produced by implantable medical device 20 and transmitted by the acoustic transmitter 22 travels through fat layer 52, skin layer 54, and a layer of air 56 prior to being received by acoustic receiver 60.

It is understood that sound waves (e.g., acoustic IMD signals) traveling though any media are subject to varying degrees of attenuation depending on the absorption and scattering characteristics of the media. The attenuation or signal degradation that occurs as an acoustic IMD signal propagates through various body tissue layers, such as fat and skin layers 52, 54, may be characterized by the following equation:

$$\alpha = 1/(2d) \cdot ln(I_0/I_d) \qquad [1]$$

where, $\alpha$ represents the lumped attenuation coefficient in units of Np/cm (Nepers per centimeter), d represents the distance traveled by the acoustic IMD signal, $I_0$ represents the intensity of the acoustic IMD signal at an initial location, and $I_d$ represents the intensity of the acoustic IMD signal after the signal has traveled a distance d.

With further reference to FIG. 3, acoustic IMD signals produced by implantable medical device 20 are subject to attenuation when traveling through fat layer 52, skin layer 54, and air layer 56 prior to being received by acoustic receiver 60. Each of the tissue and air layers 52, 54, 56 has an associated attenuation coefficient indicated in FIG. 3 as $\alpha_{fat}$, $\alpha_{skin}$, and $\alpha_{air}$, respectively. The acoustic attenuation coefficient of human skin, $\alpha_{skin}$, and fat, $\alpha_{fat}$, typically falls within a range of approximately 0.4 and 1.06 Np/cm. The acoustic attenuation coefficient in air, $\alpha_{air}$, is approximately 0.02 Np/cm at 1 KHz. It will be appreciated that degradation in various properties of an acoustic IMD signal (e.g., amplitude and phase) resulting from interaction with various body tissue layers must generally be accounted for when designing an effective acoustic telemetry approach.

An effective modulation methodology must also account for relative movement that generally occurs between implantable medical device 20 and acoustic receiver 60 during transmission of the acoustic IMD telemetry data. Movement between implantable medical device 20 and acoustic receiver 60 (i.e., receiver 60 in dashed lines) typically results from breathing and other body movement, and from inadvertent movement of acoustic receiver 60 by the holder of receiver 60.

FIG. 3 illustrates an occurrence of movement between receiver 60 relative to implantable medical device 20. More particularly, receiver 60 is depicted as being situated a distance $d_1$ away from implantable medical device 20. During transmission of acoustic IMD data, receiver 60 is moved to a distance $d_2$ away from implantable medical device 20. Receiver 60 is thus subject to displacement relative to implantable medical device 20 by a an amount $\Delta d$ during uplinking of acoustic IMD telemetry data.

In a typical application in which an implantable medical device is used to monitor one or more physiologic conditions of the heart (e.g., a pacemaker), it is reasonable to assume that an acoustic IMD signal travels through approximately 2 cm of fat 52 and skin 54 tissue before leaving the body. It is noted that in pacemaker and other heart monitoring/moderating applications, an assumption of 2 cm of total tissue thickness is considered to represent a worst case condition.

If is further assumed that the distance, d, of 2 cm may vary by as much as 20% due to relative movement between implantable medical device 20 and acoustic receiver 60, then the displacement variation, $\Delta d$, between implantable medical device 20 and acoustic receiver 60 during uplinking of acoustic IMD telemetry data is given by $\Delta d=0.4$ cm. Given a displacement variation of $\Delta d=0.4$ cm, and further assuming that the acoustic attenuation coefficient of human skin and fat falls within the range of approximately 0.4 and 1.06 Np/cm, the ratio of $I_0$ to $I_d$ in Equation [1] above may range between approximately 43% and 73% of its initial value depending on the value of the lumped attenuation coefficient, $\alpha$ (i.e., $I_d = I_0 e^{-2\Delta d\alpha} = 0.73 I_0$, where $\Delta d = 0.4$ cm and $\alpha=0.4$; and $I_d = I_0 e^{-2\Delta d\alpha} = 0.43 I_0$, where $\Delta d = 0.4$ cm and $\alpha=1.06$).

An effective modulation methodology must also account for other losses resulting from attenuation as acoustic IMD signals propagate through body tissue. For example, an acoustic IMD signal passing through an air-skin interface 56, 54, in which body tissue represents a water rich media, may be attenuated by as much as 30 dB. In order to reduce such attenuation, it is desirable that the acoustic receiver 60 be in contact with the body tissue, and preferably by use of a suitable acoustic interface, such as an ultrasound gel. Use of such an acoustic interface would limit the loss in acoustic signal strength to 20 dB under worst case conditions, indicating that 90% of the signal would be lost while passing from the skin to the external device.

Other losses which must be accounted for include receiver and transmitter transducer inefficiencies. For example, if transducer efficiency is assumed to be 50% (resulting in a 6 dB loss), a 6 dB reduction occurs as the acoustic IMD signal is transferred from the implanted transducer to the tissue, the travel distance, d, of an acoustic IMD signal is given as 2 cm, and the losses at the external device-skin interface are assumed to be 20 dB, then the overall loss in acoustic IMD signal strength would be given as (6 dB+6 dB+22.6 dB+20 dB)=54.6 dB. It is noted that the signal loss of 22.6 dB in the tissue while the acoustic IMD signal travels the distance, d, of 2 cm assumes a geometric mean for the associated attenuation coefficient, $\alpha_{mean}$, which is given by $\alpha_{mean}=(\alpha_{max}\cdot\alpha_{max})^{0.5}=(0.4\times1.06)^{0.5}=0.651$. The signal loss of 22.6 dB is thus given by $I_d/I_o = e^{-2d\alpha}$, $20\log_{10} 0.074 = -22.6$ dB.

This degree of attenuation implies that approximately 0.3% of the transmitted energy of an acoustic IMD signal would be received at the acoustic receiver end. It can be appreciated, therefore, that the acoustic IMD signal generated by the implantable medical device must be strong enough to be received by the external acoustic sensing device, as is evidenced by the overall power transfer ratio from the implantable transducer to the external acoustic sensor given by $10\log_{10}(P_{out}/P_{in})=-54$ which gives $P_{out}/P_{in}=10^{-(54/10)} \cong 10^{-6}$.

If, by way of example, a 1 mV signal is required from a piezoelectric crystal of 1 M$\Omega$ impedance, then the power of the acoustic IMD signal received by the receiver crystal must be on the order of approximately 1 pico-watts (pW) (i.e., $P_{in}=10^6 \cdot P_{out}=10^6 \cdot 10^{-12}=10^{-6}=1\,\mu W$). In many implantable medical device applications, it is believed that the minimum acoustic signal power requirements of the acoustic receiver can be satisfied. By way of example, for a pacemaker that consumes 60 microwatts ($\mu W$) continuously, 1 $\mu W$ may be expended for transmitting acoustic IMD telemetry data at a power level sufficient to meet the signal power requirements of the acoustic receiver. It is noted that 1 $\mu W$ represents less than 2% of the static power consumed by a typical implantable medical device, and that this additional 1 $\mu W$ of power is needed only when there is telemetry, which is generally very infrequent.

From the above discussion, it will be readily appreciated that care must be taken when implementing a methodology for effectively communicating acoustic IMD telemetry data transdermally. Moreover, it will be appreciated that similar care must be given when implementing a modulation scheme employed to produce a modulated IMD signal in-situ an implantable medical device, and one that produces modulated IMD signals in a form which is readily communicable over a given communication channel.

Figure 4:
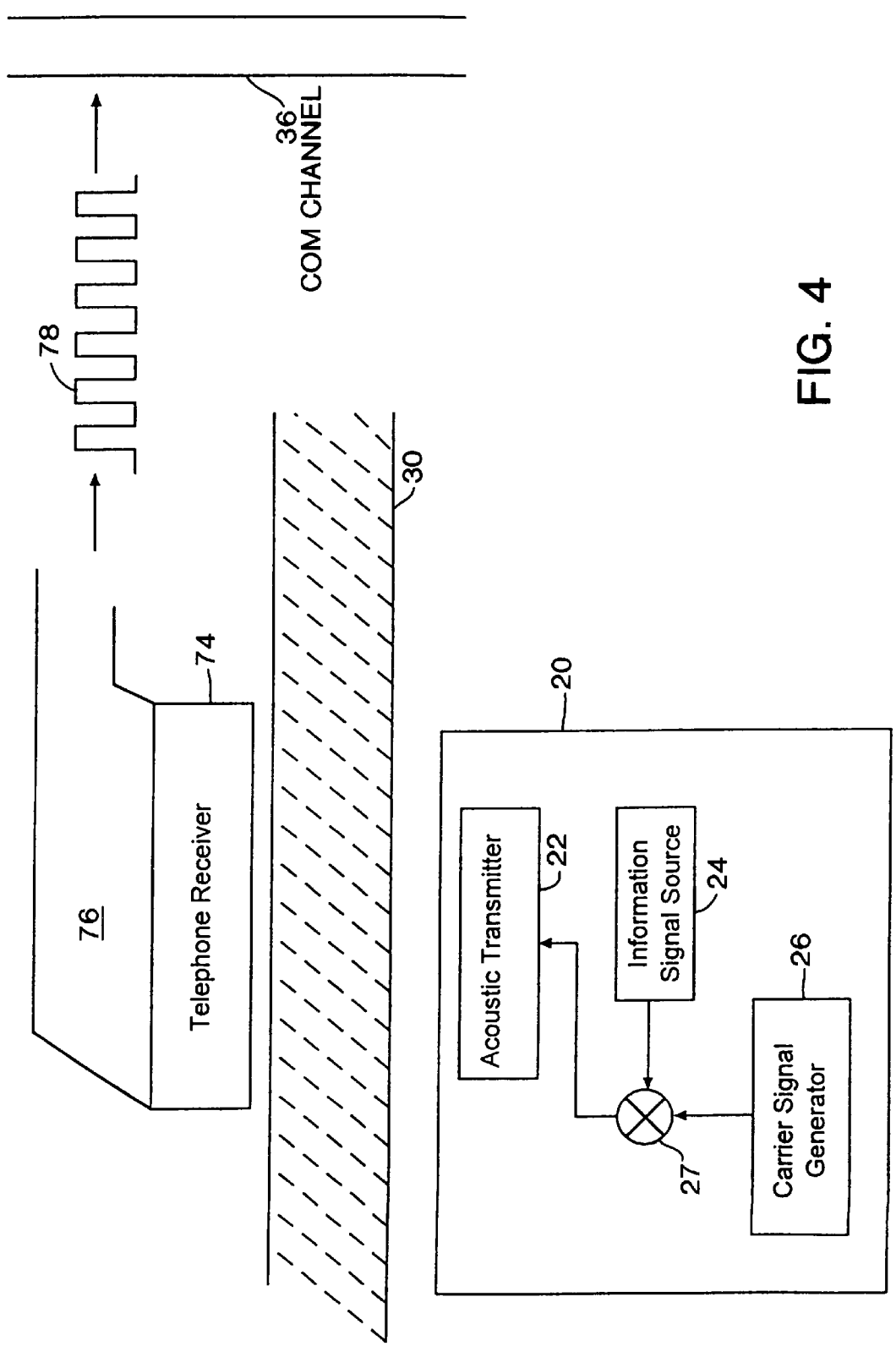
FIG. 4 is a block diagram of an implantable medical device communicating with a telephonic communication system using a telemetry approach consistent with the principles of the present invention.

In accordance with an exemplary embodiment of the present invention, and as depicted in FIG. 4, an implantable medical device 20 is employed to acoustically couple IMD information in a form readily communicable over existing digital and analog telephony systems. In accordance with this embodiment, various types of IMD information is acquired or produced by implantable medical device 20. The IMD information is converted into standard digital telephone tones and acoustically transmitted transdermally to an external acoustic receiver 76 coupled to a communication channel 36. Importantly, conversion of the IMD information to standard digital telephone tones occurs in-situ implantable medical device 20.

In one embodiment, acoustic receiver 74 represents the mouth piece of a standard telephone handset 76 held over implantable medical device 20. It will be readily appreciated that use of a standard telephone handset 76 to receive IMD telemetry data for transmission to a remote site, such as a physician's office, in accordance with the principles of the present invention substantially reduces the complexity and cost associated with the receiver portion of an IMD data communication system.

Moreover, such an implementation can be used nearly universally, as most patients provided with implantable medical devices likely have access to standard telephone equipment. Further, a patient may communicate IMD data to a remote site from any geographical location that provides standard telephone system access. As such, a patient provided with an implantable medical device is afforded increased freedom of movement, particularly during periods of evaluation and diagnosis. It is believed that the factors of ease of use, simplicity, low cost, and ubiquitous telephone system access associated with this embodiment of the present invention will promote patient participation in follow-up care which is considered by many clinicians as a critical component in the process of providing quality health care.

Further, use of standard digital telephone tones produced in accordance with the principles of the present invention provides for some measure of immunity to noise, and such tones are not subject to performance limitations that may otherwise be imposed by technical requirements of countries having differing telephone systems.

In an alternative embodiment, acoustic receiver 76 may represent an acoustic transducer provided in the programmer head of an external programming unit, such as a programmer head adapted for use with commercially available Medtronic Model 9790 Programmer. The IMD data acquired by the programmer may be stored or, alternatively, communicated in real-time to a remote site via a communication channel 36 coupled thereto.

With further reference to FIG. 4, implantable medical device 20 is shown as including several components that cooperate to produce a modulated IMD signal in a form suitable for transmission over communication channel 36. As was previously discussed, a modulated IMD signal may be produced in accordance with various known amplitude, frequency, or phase modulation techniques, and is preferably of a form which is readily communicable over communication channel 36.

In general, the frequency content of a modulated IMD signal produced by implantable medical device 20 should be band limited to frequencies appropriate for a given communication channel 36. The frequency of a carrier signal produced by carrier signal generator 26, as well as the bandwidth of the modulated IMD signal, should, therefore, be appropriately selected or adjusted in view of the available bandwidth of a particular communication channel 36. A standard telephone channel, for example, provides for an audio bandwidth of about 300 Hz to less than about 4 kHz. Other public exchange communication services may offer a greater audio bandwidth.

In applications in which transmission of modulated IMD signals is intended to be facilitated using a public exchange communication service (e.g., a publicly accessible communication system), the frequency content of a modulated IMD signal should be selected or adjusted so as to be accommodated by a particular public exchange communication system. In order to increase the bandwidth of the communication channel, one can utilize standard techniques developed by the telecommunications industry, such as single sideband modulation (SSB), convolution with pseudo-random sequences, etc., as well as other techniques which are used by newer modems, such as those supporting 54K baud rates.

A frequency shift keying (FSK) modulation methodology, by way of example, may be employed to facilitate communication of IMD telemetry data over relatively low baud rate communication channels. A telephone connection operating in conformance with a Bell 103, full duplex specification, for example, provides for a baud rate of 300 bits per second (bps). In accordance with the Bell 103 standard, an FSK modulation technique is employed by which a designated pair of audio tones are used to represent mark and space as follows: 1270 Hz (mark) and 1070 Hz (space) in one direction, 2225 Hz (mark) and 2025 Hz (space) in the other direction. A modulation approach employing an FSK methodology is well suited for communicating IMD telemetry data over relatively slow 300 bps telephonic connections.

A phase key shifting (PSK) or, more particularly, a differential phase key shifting (DPSK), modulation methodology may be employed to facilitate communication of IMD telemetry data over communication channels that accommodate relatively moderate baud rates. A modulation approach employing a PSK or DPSK methodology is well suited for communicating IMD telemetry data over 1200 and 2400 bps telephonic connections.

A telephone connection operating in conformance with a Bell 212A, 1200 baud standard, for example, provides for the transmission of "dibits" at a rate of 600 Hz. In accordance with the Bell 212A specification, a digital data stream is grouped into bit pairs, referred to as dibits. Each of the four possible dibits is transmitted as a designated phase shift of a fixed-frequency carrier signal (i.e., 00: +90°, 01: 0°, 10: 180°, and 11: −90°), with smooth transitions of phase from each transmitted dibit to the next. The phase-modulated carrier frequency is 1200 Hz in one direction, and 2400 Hz in the other direction.

To facilitate communication of IMD telemetry data over communication channels that accommodate higher baud rates, such as 9600 bits per second (bps), an amplitude modulation approach may be employed, such as an amplitude shift keying (ASK) approach. In addition, a phase modulation approach may be employed alone or in combination with an amplitude modulation approach in higher baud rate communication channels.

It is understood that modulation approaches in addition to those described herein may be employed to produce a modulated IMD signal in-situ implantable medical device 20, with due consideration given to the peculiarities of the subject communication channel and constraints imposed by the unusual operating environment of the implantable medical device 20.

With reference to FIGS. 3 and 4, and in accordance with an exemplary embodiment of the present invention, a pacemaker 20 is typically implanted subcutaneously between muscle tissue 50 and fat/skin tissue 52, 54. If it is assumed that the frequency bandwidth of communication channel 36 has an upper frequency limit of approximately 3.8 kHz (e.g., a standard telephone line), then carrier signal generator 26 may, for example, produce a carrier signal having a frequency of 2 kHz, which is appropriate for the communication channel 36 of this illustrative example.

Modulator 27, also provided in implantable medical device 20, impresses an information signal produced by information signal source 24 on the 2 kHz carrier signal and communicates a modulated IMD signal to acoustic transmitter 22. The bandwidth of the modulated IMD signal may be characterized by the following generalized equation:

$$BW \approx 2(\Delta f + f_m) \qquad [2]$$

where, BW represents the bandwidth of the modulated IMD signal in Hertz, $\Delta f$ represents a maximum frequency deviation of the modulated IMD signal, and $f_m$ represents a maximum frequency component of the information signal.

It is noted that Equation [2] above is useful for estimating the bandwidth of any general sinusoidal information signal. It can be appreciated from Equation [2] above that the bandwidth of a modulated IMD signal is a function of the frequency of the carrier signal produced by carrier signal generator 26 and of the information signal, both of which must be selected in view of the available bandwidth of a particular communication channel 36.

The modulated IMD signal provided at the output of modulator 27 is converted from electrical form to acoustic form by acoustic transmitter 22. The acoustic modulated IMD signal is transmitted from acoustic transmitter 22, through the housing wall of the implantable medical device 20, and through the body tissue media for reception by telephone receiver 74. Acoustic transmitter 22 may include a piezoelectric crystal, speaker, microphone (e.g., electret microphone), or other electrical-to-acoustic signal transducer.

In accordance with this illustrative example, the acoustic modulated IMD signals transmitted by acoustic transmitter 22 are standard digital telephone tones 78, such as tones 78 produced in conformance with a known telephony communications standard (e.g., Bell 103 or Bell 212A, for example). The acoustic IMD tones propagate through body tissue 30 and are received by mouthpiece 74 of telephone handset 76. The acoustic IMD tones are then communicated to a communication channel 36 for transmission to a remote site. It is understood that a demodulator is provided at the remote site for extracting the information signal content impressed in the acoustic IMD tones.

Figure 5:
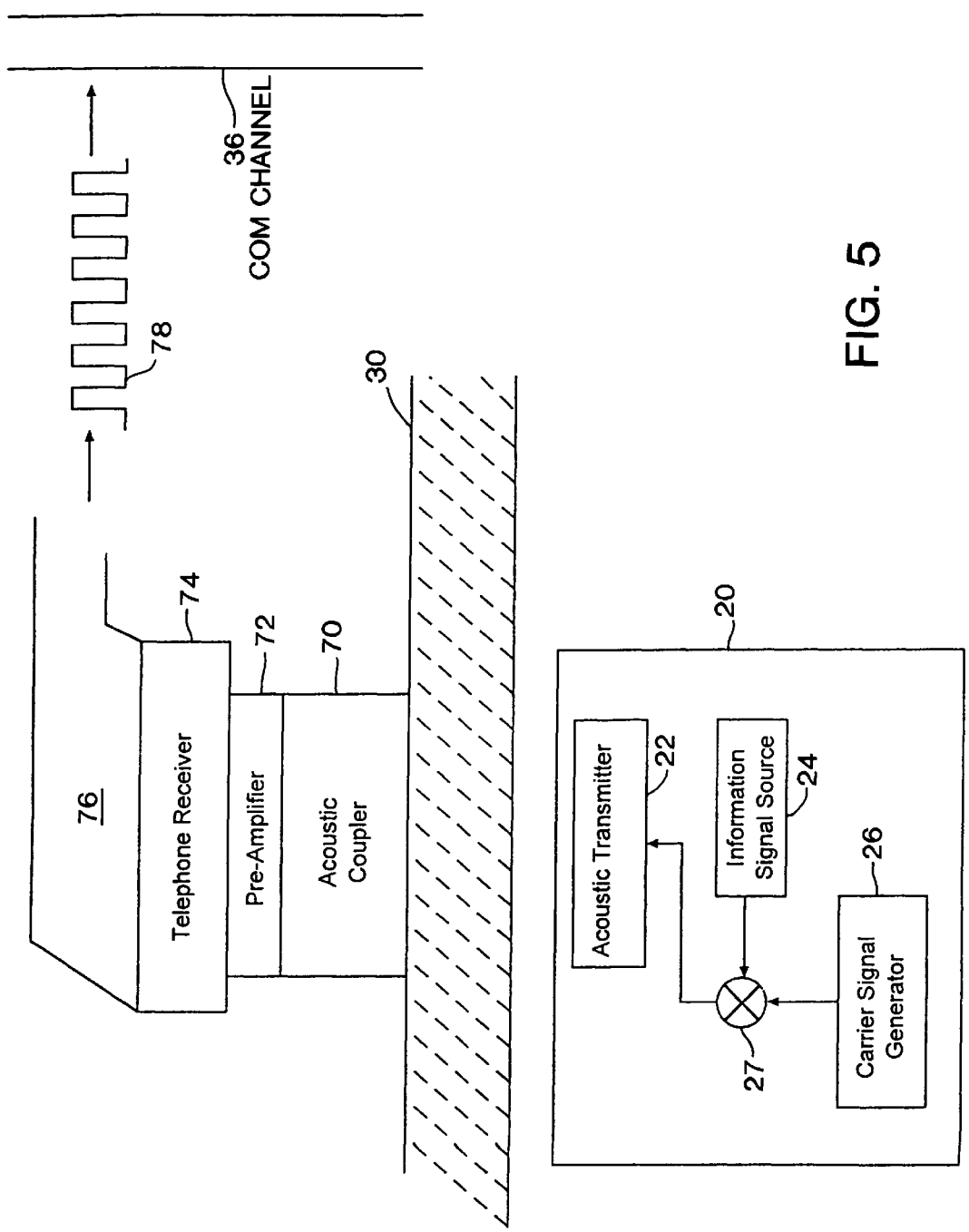
FIG. 5 is a block diagram of an implantable medical device provided with additional features for communicating with a telephonic communication system using a telemetry approach consistent with the principles of the present invention.

FIG. 5 illustrates another embodiment of the present invention in which an acoustic coupler 70 and a pre-amplifier 72 are respectively employed to enhance reception and transmission of acoustic IMD telemetry data received from implantable medical device 20. The gain and phase characteristics of pre-amplifier 72 are preferably selected to appropriately condition an attenuated acoustic IMD data signal received from implantable medical device 20 for transmission over a particular communication channel 36. Acoustic coupler 70 may include structure, alone or in combination with an ultrasound gel, that provides for enhanced coupling of acoustic signals transmitted between implantable medical device 20 and telephone receiver 74.

In the context of an embodiment which employs phase modulation, it is important to appreciate the phase delay characteristics associated with transmitting and receiving acoustic IMD signals transdermally. The velocity of acoustic IMD signals traveling through body tissue consisting primarily of muscle, fat, or skin (excluding bone tissue) is approximately 1,500 meters per second (m/sec). Given a carrier signal frequency, $f_c$, of 2 kHz and a propagation velocity, v, of 150,000 cm/sec, the wavelength, $\lambda$, of an acoustic IMD signal is given by $\lambda = v/f_c = 75$ cm. If the distance traveled by an acoustic IMD signal having a wavelength of $\lambda = 75$ cm is d=2 cm, then the phase delay, $\theta$, would be given by $\theta = 360° \cdot (2/75) = 9.6°$. If the distance variation, $\Delta d$, resulting from relative movement between the acoustic transmitter 22 in implantable medical device 20 and telephone receiver 74 changes by 20%, then the phase error, $\theta_{error}$, would be given by $\theta_{error} = 9.60° \cdot 0.2 = 1.92°$.

If the phase shift keying (e.g., PSK or DPSK) modulation methodology employed to produce a modulated IMD signal utilizes waveforms separated in phase by 45°, then a phase error of $\theta_{error} = 1.92°$ would not likely induce phase related data transmission errors. It can be appreciated from this illustrative example that the degree to which phase related errors may impact the integrity of data transmission depends on a number of application specific factors, including expected IMD signal travel distances, d, travel distance variations, $\Delta d$, wavelength/frequency of the carrier signal, signal directivity characteristics associated with the acoustic transmitter 22, and attenuation/dispersion characteristics of the body tissue media through which the acoustic IMD signals travel.

In the context of an embodiment which employs amplitude modulation, relative movement between the acoustic transmitter 22 in implantable medical device 20 and telephone receiver 74 may negatively impact the integrity of uplinked IMD telemetry data. In particular, and with further reference to FIG. 3, the amplitude of an acoustic IMD signal received by acoustic receiver 60 situated a distance $d_1$ away from implantable medical device 20 will appear to be greater in magnitude than the amplitude of the same acoustic IMD signal received by acoustic receiver 60 situated a distance $d_2$ away from implantable medical device 20, where distance $d_2$ is greater than distance $d_1$ relative to the location of implantable medical device 20.

In order to minimize ambiguities between digital states (e.g., a logical 0=0 V or $^-$1 V and a logical 1=$^+$1 V) that may arise due to relative movement between acoustic transmitter 22 in implantable medical device 20 and telephone receiver 74, it is desirable to employ an amplitude modulation methodology that provides for the production of two readily identifiable signal amplitude levels. Separating the levels of two amplitude modulated signals by an amount sufficient to reduce ambiguities when resolving the telemetry data will reduce occurrences of data transmission errors.

For example, and as previously discussed, if it is assumed that an acoustic IMD signal travels through approximately 2 cm of fat 52 and skin 54 tissue, and that the distance, d, of 2 cm may vary by as much as 20% (i.e., $\Delta d = 0.4$ cm), and assuming a lumped acoustic attenuation coefficient for human skin and fat falls of between approximately 0.4 and 1.06 Np/cm, then the ratio of $I_0$ to $I_d$ in Equation [1] above may range between approximately 43% and 73% of its initial value depending on the value of the lumped attenuation coefficient, $\alpha$. In accordance with this illustrative example, separating the levels of the two amplitude modulated IMD signals by as much as 60% can preclude or significantly reduce amplitude related data transmission errors.

The implantable medical device 20 shown in the Figures is intended to represent a wide variety of devices which may be implanted in a human body, typically for purposes of monitoring or moderating one or more physiologic conditions. By way of example, implantable medical device 20 may be an implantable cardiac pacemaker, such as one disclosed in U.S. Pat. No. 5,158,078 to Bennett et al., U.S. Pat. No. 5,312,453 to Shelton et al., or U.S. Pat. No. 5,144,949 to Olson, all of which are hereby incorporated herein by reference in their respective entireties.

Implantable medical device 20 may also be a pacemaker/cardioverter/defibrillator (PCD). The present invention may be practiced in conjunction with PCDs, such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all of which are hereby incorporated herein by reference in their respective entireties.

By way of further example, implantable medical device 20 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as that disclosed in U.S. Pat. No. 5,331,966 issued to Bennet et al., all of which are hereby incorporated herein by reference in their respective entireties. Implantable medical device 20 may also be an implantable blood oxygen sensing monitor or a hemodynamic status monitor. The present invention is believed to find wide application to any form of implantable electrical device which acquires information derived from one or more physiologic sensors, and the present invention is believed to be particularly advantageous in those contexts where a low cost telemetry design of limited complexity is employed and desired.

It will be appreciated that an implantable medical device that incorporates an acoustic telemetry production and transmission system of the present invention may also be provided with conventional electromagnetic (e.g., radio frequency) telemetry components for purposes of providing enhanced functionality and data exchange capabilities. Bi-directional communication of IMD telemetry data through use of electromagnetic signals may be accomplished in a manner disclosed in U.S. Pat. No. 4,556,063 issued to Thompson, et al., or in U.S. Pat. No. 5,312,453 issued to Wybomy, et al., both of which are incorporated herein by reference in their respective entireties.

The foregoing description of the various embodiments of the invention has been presented for the purposes of illustration and description. It is not intended to be exhaustive or to limit the invention to the precise form disclosed. For example, it will be appreciated that an implantable medical device as described herein may be provided with an acoustic receiving device for purposes of downlinking acoustic telemetry commands and information from a communication channel to the implantable medical device. In this regard, the acoustic transmitter shown in the Figures may be replaced by a suitable acoustic transceiver. Alternatively, an acoustic transmitter and an acoustic receiver may be provided in the implantable medical device.

By way of further example, various components of the acoustic telemetry production and transmission system of the present invention may be provided in separate implantable housings, and need not necessarily be provided in the same implantable medical device housing. Many modifications and variations are possible in light of the above teaching. It is intended that the scope of the invention be limited not by this detailed description, but rather by the claims appended hereto.

What is claimed is:

1. An apparatus for communicating acoustic telemetry data produced by an implantable medical device over a selectable communication channel, comprising:
    a signal generator, provided in the implantable medical device, that generates a carrier signal;
    a modulator, provided in the implantable medical device, that impresses an information signal representative of information acquired or produced by the implantable medical device on the carrier signal so as to produce a modulated information signal; and
    a controller coupled to the signal generator to control generation of the carrier signal by the signal generator and to further control generation of the modulated information signal by the modulator in accordance with the channel characteristics of the selectable communication channel; and
    a transmitter, provided at the implantable medical device, that transmits the modulated information signal as an acoustic information signal communicable over the selectable communication channel.

2. The apparatus of claim 1, wherein the acoustic information signal comprises telephonic tones.

3. The apparatus of claim 2, wherein the telephonic tones comprise a first tone representative of a first information signal state and a second tone representative of a second information signal state.

4. The apparatus of claim 1, wherein the acoustic information signal comprises digital telephonic tones each having a frequency conforming to one or more telephony standards.

5. The apparatus of claim 1, wherein the modulated information signal has a frequency content band limited by a bandwidth of the communication channel.

6. The apparatus of claim 1, wherein the transmitter comprises an electrical-to-acoustic transducer.

7. The apparatus of claim 1, wherein the transmitter comprises a piezoelectric crystal, a speaker or a microphone.

8. The apparatus of claim 1, wherein the implantable medical device is coupled to one or more physiologic sensors.

9. The apparatus of claim 1, wherein the implantable medical device comprises one of a pacemaker, a pacemaker/cardioverter/defibrillator (PCD), an oxygen sensing device, an implantable hemodynamic monitor, a muscle stimulator device or a nerve stimulator device.

10. The apparatus of claim 1, wherein the acoustic information signal is communicable over an analog communication channel, a digital communication channel, an optical communication channel, a microwave communication channel or a satellite communication channel.

11. An apparatus for communicating acoustic telemetry data produced by an implantable medical device over a selectable communication link, comprising:
    a signal generator, provided in the implantable medical device, that generates a carrier signal;
    a modulator, provided in the implantable medical device, that modulates the carrier signal using an information signal representative of information acquired or produced by the implantable medical device so as to produce a modulated information signal;
    a control circuit coupled to the signal generator to control generation of the modulated information signal to account for the bandwidth of the selectable communication link; and
    a transmitter, provided at the implantable medical device, that transmits the modulated information signal as an acoustic information signal communicable over the public exchange communication channel.

12. The apparatus of claim 11, wherein the acoustic information signal has a frequency content that is band limited by an audio bandwidth of the public exchange communication channel.

13. The apparatus of claim 11, wherein the acoustic information signal comprises telephonic tones.

14. The apparatus of claim 13, wherein the telephonic tones comprise a first tone representative of a first information signal state and a second tone representative of a second information signal state.

15. The apparatus of claim 11, wherein the acoustic information signal comprises digital telephonic tones each having a frequency conforming to one or more telephony standards.

16. The apparatus of claim 11, wherein the transmitter comprises an electrical-to-acoustic transducer.

17. The apparatus of claim 11, wherein the transmitter comprises a piezoelectric crystal, a speaker or a microphone.

18. The apparatus of claim 11, further comprising an acoustic receiver and a demodulator each provided in the implantable medical device for receiving and demodulating a modulated signal received from the public exchange communication channel.

19. The apparatus of claim 11, further comprising telemetry circuitry for facilitating communication of electromagnetic information signals between the implantable medical device and the public exchange communication system.

20. The apparatus of claim 11 wherein the acoustic information signal is communicable over an analog communication channel, a digital communication channel, an optical communication channel, a microwave communication channel or a satellite communication channel.

21. The apparatus of claim 11, wherein the implantable medical device is coupled to one or more physiologic sensors.

22. The apparatus of claim 11, wherein the implantable medical device comprises one of a pacemaker, a pacemaker/cardioverter/defibrillator (PCD), an oxygen sensing device, an implantable hemodynamic monitor, a muscle stimulator device or a nerve stimulator device.

23. A method of communicating acoustic telemetry data produced by an implantable medical device over a selected communication channel, comprising:
    generating, at the implantable medical device, a carrier signal based on the selected communication channel;

modulating, at the implantable medical device, the carrier signal using an information signal representative of information acquired or produced by the implantable medical device based on the selected communication channel; and transmitting, from the implantable medical device, the modulated information signal as an acoustic information signal communicable over the communication channel.

24. The method of claim 23, wherein transmitting the acoustic information signal comprises transmitting the acoustic information signal as telephonic tones.

25. The method of claim 24, wherein transmitting the acoustic information signal comprises transmitting the acoustic information signal as telephonic tones comprising a first tone representative of a first information signal state and a second tone representative of a second information signal state.

26. The method of claim 23, wherein transmitting the acoustic information signal comprises transmitting the acoustic information signal as digital telephonic tones each having a frequency conforming to one or more telephony standards.

27. The method of claim 23, wherein transmitting the acoustic information signal comprises transmitting the acoustic information signal over an analog communication channel, a digital communication channel, an optical communication channel, a microwave communication channel or a satellite communication channel.

28. The method of claim 23, wherein the information signal is representative of information acquired using one or more physiologic sensors coupled to the implantable medical device.

29. The method of claim 23, wherein the implantable medical device comprises one of a pacemaker, a pacemaker/cardioverter/defibrillator (PCD), an oxygen sensing device, an implantable hemodynamic monitor, a muscle stimulator device or a nerve stimulator device.

* * * * *